United States Patent [19]

Faubl

[11] 4,126,639

[45] Nov. 21, 1978

[54] PROCESS FOR 11A-DEHALOGENATION OF 11A-HALOTETRACYCLINES

[75] Inventor: Hermann Faubl, Mystic, Conn.

[73] Assignee: Pfizer Inc., New York, N.Y.

[21] Appl. No.: 743,395

[22] Filed: Nov. 19, 1976.

Related U.S. Application Data

[63] Continuation of Ser. No. 372,308, Jun. 21, 1973, abandoned.

[51] Int. Cl.$^2$ .......................................... C07C 103/22
[52] U.S. Cl. .......................... 260/559 AT; 260/654 D
[58] Field of Search ................................. 260/559 AT

[56] References Cited

U.S. PATENT DOCUMENTS

| | | | |
|---|---|---|---|
| 2,742,510 | 4/1956 | Davis | 260/654 D X |
| 3,250,809 | 5/1966 | Blackwood et al. | 260/559 AT |
| 3,413,365 | 11/1968 | Sennewald et al. | 260/654 D |
| 3,649,700 | 3/1972 | Baader et al. | 260/654 D |

FOREIGN PATENT DOCUMENTS

| | | | |
|---|---|---|---|
| 2,136,138 | 12/1972 | France | 260/559 AT |
| 1,096,942 | 12/1967 | United Kingdom | 260/654 D |

OTHER PUBLICATIONS

Borowitz et al., JACS 94:19, Sep. 20, 1972, pp. 6817–6822.

*Primary Examiner*—Allen B. Curtis
*Attorney, Agent, or Firm*—Connolly and Hutz

[57] ABSTRACT

The 11a-dehalogenation of 11a-halo-6-methylenetetracyclines by treating them with a secondary or a tertiary phosphine or a tertiary phosphite.

13 Claims, No Drawings

PROCESS FOR 11A-DEHALOGENATION OF 11A-HALOTETRACYCLINES

CROSS-REFERENCE TO RELATED APPLICATION

This application is a continuation of application Ser. No. 372,308 filed June 21, 1973 and now abandoned.

BACKGROUND OF THE INVENTION

1. Field of the Invention

This invention relates to an improved process for the 11a-dehalogenation of 11a-halo-6-demethyl-6-deoxy-6-methylenetetracyclines by treating them with a secondary or a tertiary phosphine or a tertiary phosphite.

2. Description of the Prior Art

The 11a-halo-6-demethyl-6-deoxy-6-methylenetetracyclines, referred to herein for convenience as 11-a-halo-6-methylenetetracyclines, form an important class of intermediates for further synthesis of tetracycline-type antibiotics, such as the valuable and widely used antibiotics 6-demethyl-6-deoxy-6-methylene-5-hydroxytetracycline and 6α-deoxy-5-hydroxytetracycline which are prepared from 11a-chloro-6-demethyl-6-deoxy-6-methylene-5-hydroxytetracycline; the former by 11a-dehalogenation and the latter by 11a-dehalogenation and reduction of the 6-methylene group.

The previously known methods for 11a-dehalogenation of 11a-halotetracyclines, including 11a-halo-6-methylenetetracyclines, are discussed in U.S. Pat. No. 3,043,875, issued July 10, 1962. These methods comprise a variety of reactions, such as treatment of the 11a-halotetracyclines:

(a) With dilute aqueous hydriodic acid,
(b) With zinc metal in the presence of a proton donor, such as acetic acid,
(c) In the case of 11a-bromo and 11a-iodo compounds, by boiling the product with a solvent capable of reacting with bromine or iodine (acetone, methanol, etc.),
(d) Alternatively, treatment with sodium iodide in organic solvent, followed by treatment of the resultant iodo compound with metallic zinc,
(e) Treatment with metal sulfites and hydrosulfites, particularly the alkali metal (Na, K, Li) salts are useful, and
(f) By catalytic hydrogenation of the 11a-halotetracycline in a reaction-inert medium with hydrogen gas in the presence of a noble metal catalyst.

A further procedure, described in French Pat. No. 2,136,138, comprises electrochemical dehalogenation.

The dehalogenation of α-halo organo compounds, e.g., ketones and nitriles, by means of tertiary phosphines is reported by Borowitz et al., Tetrahedron Letters, No. 11, 471–4 (1962), Partos et al., J. Am. Chem. Soc. 87, 5068–75 (1965) and Borowitz et al., J. Org. Chem. 33, 3686–90 (1968). The use of diphenylphosphine, a secondary phosphine, as dehalogenating agent for α-haloketones is described by Borowitz et al., J. Org. Chem. 34, 2687–92 (1969). Triethylphosphite has been shown by Pudovik et al., Zhur, Obschei Khim 28, 1496–1500 (1958), (C.A. 53, 216 g) and Kreutzkamp et al., Ann. 609, 39 (1957), to function as a dehalogenating agent.

These known methods of 11a-dehalogenation of 11a-halotetracyclines are subject to disadvantages arising from the use of expensive catalysts (method f) or equipment (electrochemical dehalogenation); reaction mixtures which are frequently difficult to separate from by-products and, frequently, incomplete conversions to 11a-dehalogenated product.

SUMMARY OF THE INVENTION

It has now been found that 11a-halotetracyclines can be readily dehalogenated by contacting them with a secondary or a tertiary phosphine or a tertiary phosphite. Major interest exists in 11a-halo-6-methylenetetracyclines of the formula shown below because of the general importance of the 11a-dehalogenated analogs thereof as antibacterial agents and intermediates:

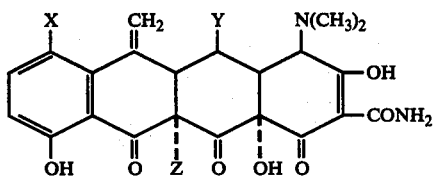

and the acid addition salts thereof wherein X is selected from the group consisting of hydrogen and chloro; Y is selected from the group consisting of hydrogen, hydroxy and alkanoyloxy, wherein the alkanoyloxy group has from 1 to 8 carbon atoms; and Z is selected from the group consisting of chloro and bromo.

Particular interest resides in those 11a-halo-6-methylenetetracyclines of the above formula wherein Z is chloro for the above-mentioned reason, plus the fact that the 11a-chloro derivatives are conveniently prepared and, because of their stability relative to that of the corresponding 11a-bromo and 11a-iodo derivatives, easily isolated and stored without decomposition.

Special interest exists in 11a-chloro-6-demethyl-6-deoxy-6-methylenetetracycline (X = H, Y = OH, Z = Cl) which serves as intermediate for the production of 6α-deoxy-5-hydroxy-tetracycline, a broad spectrum antibacterial agent of great value to mankind.

DETAILED DESCRIPTION OF THE INVENTION

The process of this invention comprises treating an 11a-halotetracycline of the above formula or an acid addition salt thereof in a suitable solvent with a secondary or tertiary phosphine or a tertiary phosphite. Suitable solvents are hydroxylic-containing solvents such as water, alkanoic acids and substituted alkanoic acids wherein the substituent is selected from the group consisting of lower alkoxy, hydroxy or cyano; alcohols and substituted alcohols wherein the substituent is selected from the group consisting of hydroxy and lower alkoxy. Favored solvents are water, methanol, ethanol and mixtures of these. Further, mixtures of such hydroxylic solvents with non-hydroxylic solvents such as lower alkyl esters of lower alkanoic acids (methyl acetate, ethyl acetate, methyl propionate), tetrahydrofuran, dioxane, aromatic hydrocarbons (e.g. benzene, toluene, xylene), ketones (e.g. acetone, methyl isobutyl ketone), and di(lower alkyl)alkanoic acid amides (e.g. N,N-dimethylformamide, N,N-dimethylacetamide) can be used. Additionally, when the phosphine or phosphite dehalogenating agent is a liquid at the temperature of the reaction, it can serve as both reactant and solvent.

The temperature of the reaction is not critical. The reaction is operative over a wide temperature range, that is, from about 20° C. to the boiling point of the solvent system when using secondary or tertiary phosphines as dehalogenating agents. Lower temperatures can be used but are of no advantage since the reaction appears to be relatively slow at lower temperatures. The favored reaction temperature, from the standpoint of convenience, is room temperature, that is, from about 20° C. to about 30° C. Higher temperatures have, of course, the advantage of accelerating the reaction and the disadvantage, albeit relatively minor, of requiring greater caution in operating the reaction on a large scale when volatile solvents are employed. When using tertiary phosphites as dehalogenating agents, temperatures of from about 50° C. to the boiling point of the solvent system are operative. The reaction is so slow below 50° C. as not to be practical.

The 11a-halo-6-methylenetetracycline reactants can be used in amphoteric or base form, or as an acid addition salt. In practice, they are generally used as an acid addition salt since this is the form in which they are normally isolated. The nature of the acid addition salt is immaterial to the reaction. The hydrochloride and p-toluenesulfonate salts are the salt forms in which the 11a-halo-6-methylenetetracyclines are generally isolated, especially in large-scale preparations and are, therefore, the form in which the 11a-halo-6-methylenetetracyclines are usually used.

The 11a-halo-6-methylenetetracycline need not dissolve completely in the solvent medium used. The reaction proceeds satisfactorily in mixtures in which the 11a-halo-6-methylenetetracycline is only partially soluble.

The phosphines of value in the present invention are secondary and tertiary phosphines of the formula

  I wherein each of $R_1$ and $R_2$ is selected from the group consisting of alkyl of from 1 to 10 carbon atoms, cyclohexyl, benzyl and aryl wherein aryl is selected from the group consisting of phenyl, methyl substituted phenyl, methoxy substituted phenyl and halo substituted phenyl; and $R_3$ is selected from the group consisting of hydrogen and $R_1$.

Principal interest exists in the tertiary aryl phosphines because of the favorable yields afforded by such agents.

The phosphites of interest to the process of this invention have the formula

  II wherein $R_4$, $R_5$ and $R_6$ is selected from the group consisting of alkyl of from 1 to 10 carbon atoms, cyclohexyl, benzyl and aryl wherein aryl is selected from the group consisting of phenyl, methyl substituted phenyl, methoxy substituted phenyl and halo substituted phenyl.

In this series of dehalogenating agents those wherein the variables $R_4$, $R_5$ and $R_6$ are lower alkyl are favored because of their ready availability.

The term "lower alkyl" and "lower alkoxy" as used herein are intended to include alkyl and alkoxy groups of from 1 up to and including 4 carbon atoms.

The 11a-halo-6-methylenetetracycline reactant and the dehalogenating agent are generally reacted in a molar proportion of from about 1:1 to about 1:3. The favored molar ratio of 11a-halo-6-methylenetetracycline compound to dehalogenating agent is from about 1:1 to about 1:1.5. Higher ratios can be used but serve no useful purpose. The use of less than one mole of dehalogenating agent per mole of 11a-halo compound is not desired since it gives incomplete reaction and poor yields.

The products are isolated by methods commonly used for isolation of 6-methylenetetracyclines, such as extraction and precipitation. The dehalogenating agents and the products to which they are converted do not appear to interfere in the isolation procedures.

Secondary phosphites of the formula $(R_4O)(R_5O)$-POM wherein $R_4$ and $R_5$ are as previously defined, and M is sodium or potassium; and phosphonites such as dibutylphenylphosphonite and ethyldiphenylphosphonite are also effective as dehalogenating agents in the same manner as are the tertiary phosphites.

EXAMPLE I

6-Demethyl-6-Deoxy-6-Methylene-5-Hydroxytetracycline p-Toluenesulfonate

A. To a stirred solution of 11a-chloro-6-demethyl-6-deoxy-6-methylene-5-hydroxytetracycline p-toluenesulfonate (6.4295 g., 10 mM) in N,N-dimethylformamide (12 ml.) and benzene (7 ml.) at room temperature is added triphenylphosphine (3.9343 g., 15 mM). The mixture becomes warm and is heated at 90° C. for 50 minutes. It is then cooled and poured into benzene (375 ml.). The yellow solid, the dehalogenated product, which precipitates is removed by filtration, washed with diethyl ether and air-dried (4.275 g., 70.6%). It is identified by NMR as 6-demethyl-6-deoxy-6-methylene-5-hydroxytetracycline.

The filtrate and wash solutions are combined, wash successively with water (2 × 100 ml.) and brine (1 × 50 ml.) and dried with anhydrous sodium sulfate. Removal of the solvent affords a brownish residue (3.306 g.). The residue is dissolved in chloroform and chromatographed on a silica gel column. Elution with chloroform followed by 15% ethyl acetate/chloroform and evaporation of the eluate gives triphenylphosphine oxide in 93% yield. (M.P. 155°-157° C.)

Based upon the yield of triphenylphosphine oxide recovered, conversion of the 11a-chloro compound to the deschloro analog is also at least 93%. The fact that less than 93% yield of 11a-deshalo analog is isolated is attributable to incomplete precipitation of the product by benzene.

B. Repetition of this procedure but without the application of external heat to the reaction mixture produces substantially the same results.

EXAMPLE II

The procedure of Example I-B is repeated but using the dehalogenating agents listed below in place of triphenylphosphine. In each instance, 6-demethyl-6-deoxy-6-methylene-5-hydroxytetracycline is produced:

| | |
|---|---|
| $(C_7H_7)_3P$ | $(C_6H_5)_2PH$ |
| $(2-ClC_6H_4)_3P$ | $(2-ClC_6H_4)_2PH$ |
| $(3-ClC_6H_4)_3P$ | $(2-CH_3C_6H_4)_2PH$ |
| $(4-ClC_6H_4)_3P$ | $(C_6H_5)(4-CH_3C_6H_4)PH$ |
| $(2-CH_3OC_6H_4)_3P$ | $(2-CH_3OC_6H_4)_2PH$ |
| $(3-CH_3C_6H_4)_3P$ | $(CH_3)_2(C_7H_7)P$ |
| $(4-CH_3C_6H_4)_3P$ | $(CH_3)_2(4-CH_3OC_6H_4)P$ |
| $(C_6H_{11})_3P$ | $(4-CH_3C_6H_4)_2(CH_3)P$ |
| $(CH_3)_3P$ | $(C_6H_{13})_3P$ |
| $(C_{10}H_{21})_3P$ | $(C_2H_5)(C_6H_5)_2P$ |
| $(C_2H_5)_2(C_6H_5)P$ | $(C_{10}H_{21})(C_6H_5)_2P$ |

-continued

| | |
|---|---|
| $(C_2H_5)_2(4-CH_3OC_6H_4)_2P$ | $(C_6H_{11})_2(C_6H_5)P$ |
| $(4-BrC_6H_4)_3P$ | $(4-FC_6H_4)_3P$ |
| $(CH_3)_2PH$ | $(n-C_4H_9)_2PH$ |

EXAMPLE III

6-Demethyl-6-Deoxy-6-Methylene-5-Hydroxytetracycline Sulfosalicylate

A. A methanol solution of tri(n-butyl)phosphine (0.62 ml. of 5 mM) is added at room temperature to a solution of 11a-chloro-6-demethyl-6-deoxy-6-methylene-5-hydroxytetracycline hydrochloride (1.536 g., 3.1 mM) in methanol (15 ml.) and the mixture stirred for 20 hours. One-third of the reaction mixture is treated with a solution of sulfosalicylic acid (1 ml. of 1 M aqueous solution), the mixture stirred for 15 minutes and then filtered to recover the title compound (0.424 g., 61%), identified by ultraviolet, infrared and nuclear magnetic resonance spectroscopy.

The filtrate is evaporated under reduced pressure and the residue partitioned between water and chloroform. The aqueous phase is separated, extracted with chloroform (2 × 10 ml.) and the combined extracts decolorized, dried (Na$_2$SO$_4$) and evaporated under reduced pressure. The residue, a viscous oil, crystallized upon storage in a high vacuum (0.135 g., 62% yield).

Mass spectra showed it to be tri(n-butyl)phosphine oxide.

B. Repetition of this procedure but using triphenylphosphine in place of tri(n-butyl)phosphine produces a similar result.

EXAMPLE IV

6-Demethyl-6-Deoxy-6-Methylene-5-Hydroxytetracycline Hydrochloride

The remaining two-thirds of the reaction mixture of Example III, upon standing for three days, deposited a yellow solid. The solid is filtered off, washed with benzene and air-dried (0.658 g., 69% yield of the title compound identified by thin layer chromatography in the system tetrahydrofuran/water (95/5) on silica gel plates at pH 6.0).

EXAMPLE V

6-Demethyl-6-Deoxy-6-Methylene-5-Hydroxytetracycline Sulfosalicylate

A. To a solution of 11a-chloro-6-demethyl-6-deoxy-6-methylene-5-hydroxytetracycline hydrochloride (2.052 g., 4.0 mM) in acetone (10 ml.)-water (2 ml.) at room temperature is added tris(4-methoxyphenyl)phosphine (1.61 g., 4.2 mM) over a 5-minute period. A slight exothermic reaction occurs and a water bath is used to maintain the temperature at room temperature. After stirring for 1 hour, the reaction mixture is concentrated under reduced pressure to remove the acetone. Methanol (20 ml.) is added followed by a 10% methanolic solution of sulfosalicylic acid (15 ml.). The mixture is stirred for 4 hours and then cooled to about 15° C. The solid product is filtered off, washed with cold methanol (2 × 5 ml.) and dried in vacuo (2.54 g. of title product, 96.2%). It is identical to the product of Example III.

B. Repetition of this procedure but using molar ratios of 11a-chloro reactant to phosphine of 1:2, 1:3 and 1:5 affords substantially the same results.

EXAMPLE VI

Following the procedure of Example V, the 11a-halo-6-methylenetetracyclines listed below are converted to the corresponding 11a-deshalo-6-methylenetetracyclines:

| 6-Methylenetetracycline | Salt |
|---|---|
| 7,11a-dichloro-5-hydroxy | hydrochloride |
| 11a-chloro- | hydrochloride |
| 7,11a-dichloro- | hydrochloride |
| 11a-chloro-5-hydroxy | — |
| 11a-chloro-5-hydroxy | hydrofluoride |
| 11a-chloro-5-hydroxy | acetate |
| 11a-chloro- | citrate |
| 7,11a-dichloro | benzoate |
| 11a-bromo- | hydrobromide |
| 7-chloro-11a-bromo | hydrobromide |
| 11a-chloro-5-acetoxy | tosylate |
| 11a-chloro-5-formyloxy | tosylate |
| 11a-chloro-5-butyryloxy | tosylate |
| 11a-chloro-5-octanoyloxy | tosylate |
| 7,11a-dichloro-5-acetoxy | tosylate |
| 7,11a-dichloro-5-hexanoyloxy | hydrochloride |

EXAMPLE VII

6-Demethyl-6-Deoxy-6-Methylene-5-Hydroxytetracycline Hydrochloride

The procedure of Example V-A is repeated but using 4.2 mM of dimethylphenylphosphine in place of tris(4-methoxyphenyl)phosphine affords 1.598 g. (84%) of the title product.

EXAMPLE VIII

6-Demethyl-6-Deoxy-6-Methylene-5-Hydroxytetracycline Sulfosalicylate via Triethyl Phosphite Dehalogenation)

A mixture of triethyl phosphite (3.82 g., 23.0 mM) and 11a-chloro-6-demethyl-6-deoxy-6-methylene-5-hydroxytetracycline p-toluenesulfonate (3.214 g., 4.51 mM) in ethanol (34 ml.) is heated to reflux for 1 hour. It is then cooled to room temperature and stirred for 3 hours after which it is chilled to 0° C. and the solid removed by filtration. The filtrate is treated with sulfosalicylic acid (20 ml. of 10% aqueous solution) and stirred at room temperature overnight. The title product is recovered by filtration, washed with cold methanol and dried in vacuo (2.163 g., 73%).

An additional 0.148 g. is recovered from the filtrate upon removal of the alcohol. (Total yield: 2.311 g., 78%.) It is identified by its ultraviolet, infrared and nuclear magnetic resonance spectra.

EXAMPLE IX

The procedure of Example VIII is repeated but using the dehalogenating agents listed below in place of triethylphosphite. In each instance, 6-demethyl-6-deoxy-6-methylene-5-hydroxytetracycline is produced.

$(CH_3O)_3P$
$(C_6H_5O_3)P$
$(i-C_4H_9O)_3P$
$(C_6H_5O)_2(n-C_4H_9O)P$
$(4-ClC_6H_4)_3P$
$(2-CH_3OC_6H_4O)_3P$
$(4-CH_3C_6H_4O)_3P$
$(C_6H_{11}O)_3P$
$(CH_3O)_2(C_6H_5O)P$ (CH₃O)(C₆H₅O)₂P
(C₁₀H₂₁O)₃P

EXAMPLE X

6-Demethyl-6-Deoxy-6-Methylene-5-Hydroxytetracycline Sulfosalicylate

A mixture of 11a-chloro-6-demethyl-6-deoxy-6-methylene-5-hydroxytetracycline p-toluenesulfonate (2.927 g., 4.51 mM), methanol (30 ml.), water (4 ml.) and triphenylphosphine (1.205 g., 4.60 mM) is stirred under an atmosphere of nitrogen at room temperature for 3 hours. Methanol (18 ml.) and an aqueous solution of sulfosalicylic acid (20 ml. of 10% solution) are added to the mixture which is thoroughly stirred and allowed to crystallize by standing for 18 hours. The product is filtered off, washed with cold methanol (0°-5° C.) and dried. Yield = 2.671 g., 88% yield.

EXAMPLE XI

Diphenylphosphine (27.21 mg. 0.1575 mM) is added to a solution of 11a-chloro-6-demethyl-6-deoxy-6-methylene-5-hydroxytetracycline hydrochloride (25.7 mg., 0.050 mM) in methanol (1.5 ml.) under an atmosphere of nitrogen. The mixture is stirred for 28 hours and then evaporated to dryness in vacuo. The oily residue is washed with ether (3 × 1 ml.) and then dissolved in methanol (0.32 ml.). An aqueous solution of sulfosalicylic acid (0.16 ml. of 10% solution) is added and the mixture stirred overnight. The mixture is warmed to 38°-40° C. and the liquid phase evaporated to about 0.5 ml. by exposing the warm mixture to a stream of nitrogen gas. It is then centrifuged, the supernatant pipetted off and the crystals washed with ether (1 ml.). The supernatant solution is then passed through a column of Amberlite IR-45 (hydroxide form of a weakly basic anion exchange resin available from Rohm and Haas Co.). The ion exchange resin is slurried in 1N methanolic hydrogen chloride, the column packed and rinsed thoroughly with methanol. The supernatant solution is passed through the column, the eluate collected and evaporated to dryness is vacuo. The residue is taken up in the minimum volume of ethanol and the solution evaporated under reduced pressure to thoroughly dry the product. Yield = 15 mg., 45.4%

What is claimed is:

1. A process for the preparation of 6-demethyl-6-deoxy-6-methylenetetracycline having the formula or an acid addition salt thereof where:
Y = H, chloro
R = H, OH, —O—CO—R'
R' = alkyl group containing from 1 to 17 C. atoms,
by means of the reductive dehalogenation effected with the employment of tertiary phosphines, of 11a-halo-6-demethyl-6-deoxy-6-methylenetetracycline having the formula or an acid addition salt thereof where:
X = chloro, bromo
Y = H, chloro
R = H, —OH, —O—COR'
R' = alkyl group containing from 1 to 7 C. atoms, in polar solvents selected from the group consisting of alcohols containing at least one hydroxy group, lower alkoxy substituted alcohols or mixtures of said alcohols with dioxane, tetrahydrofuran, N,N-dimethylformamide and acetone, at temperatures comprised between 20° C. and the boiling point of said product.

2. A process according to claim 1, characterized by the fact that the reagent is triphenylphosphine.

3. The process according to claim 1, wherein the reaction period is at least 50 minutes.

4. A process which comprises contacting an 11a-halo-6-methylenetetracycline compound in a reaction-inert solvent with at least an equimolar amount of a phosphorous compound selected from the group consisting of secondary phosphines, tertiary phosphines and tertiary phosphites.

5. A process according to claim 4 wherein the phosphorous compound is selected from the group consisting of $$R_1R_2R_3P \quad \text{and} \quad \begin{matrix} R_4O \\ R_5O-P \\ R_6O \end{matrix}$$

I             II wherein
each of $R_1$, $R_2$, $R_4$, $R_5$ and $R_6$ is selected from the group consisting of alkyl of from 1 to 10 carbon atoms, cyclohexyl, benzyl and aryl wherein aryl is selected from the group consisting of phenyl, methyl substituted phenyl, methoxy substituted phenyl and halo substituted phenyl; and
$R_3$ is selected from the group consisting of hydrogen and $R_1$.

6. A process according to claim 5 wherein 11a-halo-6-methylenetetracycline is of the formula and the acid addition salts thereof wherein
X is selected from the group consisting of hydrogen and chloro;

Y is selected from the group consisting of hydrogen, hydroxy and alkanoyloxy wherein the alkanoyloxy group has from 1 to 8 carbon atoms; and Z is selected from the group consisting of chloro and bromo.

7. A process according to claim 6 wherein Z is chloro.

8. A process according to claim 7 wherein Y is hydroxy and X is hydrogen.

9. A process according to claim 7 wherein Y is hydroxy and X is chloro.

10. A process according to claim 8 wherein the phosphorous compound is of the formula I wherein $R_3$ is $R_1$.

11. A process according to claim 10 wherein each of $R_1$, $R_2$ and $R_3$ is alkyl.

12. A process according to claim 10 wherein each of $R_1$, $R_2$ and $R_3$ is aryl.

13. A process according to claim 12 wherein each of $R_1$, $R_2$ and $R_3$ is phenyl.

* * * * *